United States Patent [19]

Harandi et al.

[11] Patent Number: 5,167,937
[45] Date of Patent: Dec. 1, 1992

[54] PRODUCTION OF GASOLINE AND ETHER FROM METHANOL WITH FEEDSTOCK EXTRACTION

[75] Inventors: Mohsen N. Harandi, Lawrenceville; Hartley Owen, Belle Mead, both of N.J.

[73] Assignee: Mobil Oil Corporation, Fairfax, Va.

[21] Appl. No.: 699,550

[22] Filed: May 14, 1991

Related U.S. Application Data

[63] Continuation-in-part of Ser. No. 358,097, May 30, 1989, Pat. No. 5,047,070, which is a continuation-in-part of Ser. No. 308,072, Feb. 9, 1989, Pat. No. 5,009,859, which is a continuation-in-part of Ser. No. 179,725, Apr. 11, 1988, Pat. No. 4,827,045.

[30] Foreign Application Priority Data

Apr. 23, 1990 [AU] Australia .......................... 55298/90
Apr. 23, 1990 [EP] European Pat. Off. ........ 90906693.8

[51] Int. Cl.$^5$ ............................................. B01J 8/04
[52] U.S. Cl. .................... 422/190; 422/187; 422/189; 422/234; 422/256; 203/DIG. 6
[58] Field of Search ............... 422/146, 187, 190, 189, 422/234, 256; 568/697; 203/DIG. 6

[56] References Cited

U.S. PATENT DOCUMENTS

| 4,560,537 | 12/1985 | Tabak | 422/190 |
| 4,678,645 | 7/1987 | Chang et al. | 422/190 |
| 4,684,757 | 8/1987 | Avidan et al. | 585/331 |
| 4,689,205 | 8/1987 | Gould et al. | 422/142 |
| 4,767,604 | 8/1988 | Owen et al. | 422/190 |
| 4,788,364 | 11/1988 | Harandi | 585/312 |
| 4,831,195 | 5/1989 | Harandi et al. | 568/697 |
| 4,832,920 | 5/1989 | Owen et al. | 422/190 |
| 4,925,455 | 5/1990 | Harandi et al. | 44/77 |
| 4,975,097 | 12/1990 | Harandi et al. | 44/77 |
| 5,026,529 | 6/1991 | Harandi et al. | 422/190 |
| 5,045,287 | 9/1991 | Harandi et al. | 422/142 |
| 5,064,623 | 11/1991 | Harandi et al. | 422/190 |

Primary Examiner—Robert J. Warden
Assistant Examiner—Christopher Y. Kim
Attorney, Agent, or Firm—Alexander J. McKillop; Charles J. Speciale; L. G. Wise

[57] ABSTRACT

An integrated reactor system for converting methanol or the like to ether and gasoline hydrocarbons. Alcohol feedstock containing water is extracted with olefinic liquid and reacted catalytically to produce tertiary ether. Unreacted alcohol and olefin vapor separated from etherification effluent is converted along with aqueous alcoholic raffinate in a zeolite catalysis step to produce gasoline and paraffinic intermediate. By dehydrogenating the $C_3$–$C_5$ paraffins, an olefinic liquid rich in isoalkenes is obtained for recycle to the extractor as solvent for alcohol feedstock.

4 Claims, 1 Drawing Sheet

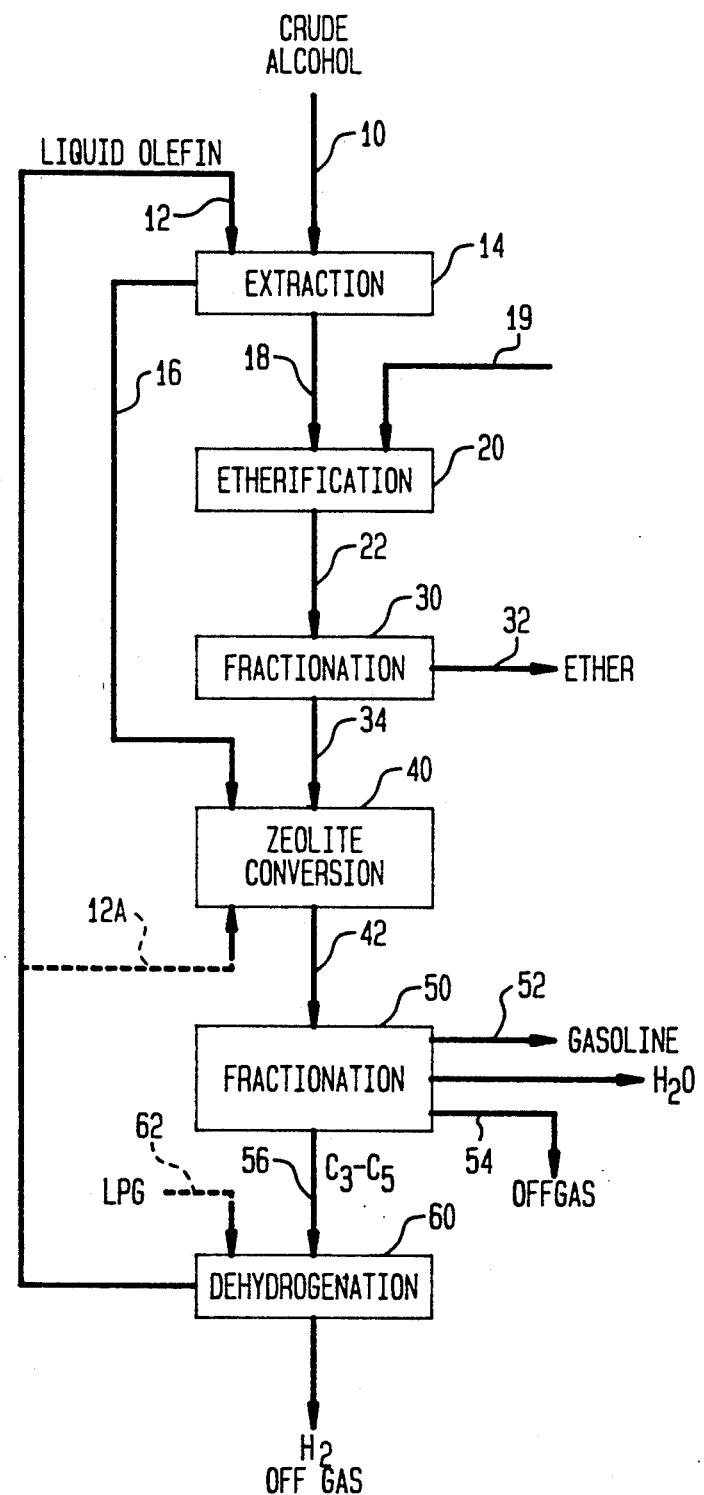

PRODUCTION OF GASOLINE AND ETHER FROM METHANOL WITH FEEDSTOCK EXTRACTION

REFERENCE TO COPENDING APPLICATION

This application is a continuation-in-part of U.S. patent Application Ser. No. 07/358,097 filed May 30 1989 (now U.S. Pat. No. 5,047,070); which is a continuation-in-part of application Ser. No. 308,072 filed Feb. 9, 1989 (now U.S. Pat. No. 5,009,859); which is a continuation-in-part of Ser. No. 179,725, filed Apr. 11, 1988 (now U.S. Pat. No. 4,827,045), incorporated by reference.

BACKGROUND OF THE INVENTION

This invention relates to integrated reactor and extraction equipment and operating techniques for converting crude methanol or similar lower aliphatic alcohols to high octane gasoline and methyl tertiary-alkyl ethers, such as MTBE. In particular, this invention relates to an improvement in utilizing methanol-to-gasoline (MTG) operating systems for converting crude methanol to valuable products by etherifying lower branched olefins, such as $C_4$-$C_5$ normally liquid iso-olefins.

Technical progress of the commercial methanol-to-gasoline (MTG) process has provided an important synthetic fuel source. Also, there has been considerable development of processes synthetic alkyl tertiary-alkyl ethers as octane boosters in place of conventional lead additives in gasoline. The etherification processes for the production of methyl tertiary alkyl ethers, in particular methyl t-butyl ether (MTBE) and t-amyl methyl ether (TAME) have been the focus of considerable research attention to resolve certain limitations in the etherification process with respect to the opportunity to drive the equilibrium dependent etherification reaction to completion by conducting etherification in the presence of excess methanol. It is known that recovering unreacted methanol by conventional separation and extraction techniques imposes severe economic burdens on the etherification process.

Recognizing the common feedstock (e.g.—methanol) for the synthetic production of gasoline as well as the production of methyl tertiary alkyl octane boosting ethers, research workers have endeavored to combine these processes in a manner to provide a synergistically beneficial integrated process.

It is known that isobutylene and other isoalkenes produced by hydrocarbon cracking may be reacted with methanol, ethanol, isopropanol and other lower aliphatic primary and secondary alcohols over an acidic catalyst to provide tertiary ethers. Methanol is considered the most important $C_1$-$C_4$ oxygenate feedstock because of its widespread availability and low cost. Therefore, primary emphasis herein is placed on MTBE and TAME. Methanol may be readily obtained from coal by gasification to synthesis gas and conversion of the synthesis gas to methanol by well-established industrial processes. As an alternative, the methanol may be obtained from natural gas by other conventional processes, such as steam reforming or partial oxidation to make the intermediate syngas. Crude methanol from such processes usually contains a significant amount of water, usually in the range of 4 to 20 wt. %; however, the present invention is useful for removing water in lesser amounts or greater.

It is an object of the present invention to provide a novel and economic technique for removing excess water from crude methanol feedstocks, including novel reactor systems and equipment for treating oxygenate feedstocks prior to etherification and disposing of raffinate containing methanol. It has been discovered that aqueous methanol streams, such as etherification feedstock extraction raffinate can be economically upgraded to valuable gasoline product by catalytic conversion concurrently with hydrocarbons.

SUMMARY OF THE INVENTION

A continuous reactor system is provided for converting crude lower alkyl alcohol to lower alkyl t-alkyl ethers. The unit operations comprise:

(a) extraction means for contacting crude aqueous alcohol feedstock containing with a liquid hydrocarbon extraction solvent rich in $C_4^+$ iso-alkene hydrocarbon under extraction conditions favorable to selective extraction of the alcohol, thereby providing an extract liquid stream rich in alcohol and an aqueous raffinate stream lean in alcohol;

(b) primary etherification reactor means operatively connected to receive the extract liquid stream for charging liquid hydrocarbon extractant and extracted methanol substantially free of water to a first catalytic reaction zone containing acid etherification catalyst for converting alcohol and iso-alkene hydrocarbon to predominantly lower alkyl t-alkyl ether;

(c) fractionation means for separating etherification effluent from reactor (b) to recover unreacted alcohol and light olefinic hydrocarbon overhead vapor and to recover liquid product containing ether product;

(d) secondary catalytic reactor means for upgrading olefinic overhead vapor from fractionator (c) to provide liquid hydrocarbon product; and (e) means for charging at least a portion of said aqueous raffinate stream from extraction means (a) for conversion of alcohol to hydrocarbons concurrently with olefin upgrading in reactor (d). In a typical reactor system the primary reactor means includes acid etherification catalyst, such as ion exchange resin, and the secondary reactor means contains acid medium pore zeolite catalyst.

These and other objects and features of the invention will be understood from the following description and in the drawing.

DRAWING

The drawing is a schematic methanol extraction and etherification system flowsheet depicting the present invention.

DETAILED DESCRIPTION

Typical feedstock materials for etherification reactions include olefinic streams, such as FCC light naphtha and butenes rich in iso-olefins. Typically, these aliphatic streams are produced in petroleum refineries by catalytic cracking of gas oil or the like. The crude methanol commercially available from syngas processes may contain, for instance 4 to 17 wt. % water, which must be removed, preferably to a methanol purity of about 99.8 wt. %. It has been found that more than 75% of crude feedstock methanol can be recovered by liquid extraction with light olefinic liquid extraction solvent, such as propylene, iso-butylenes, iso-amylenes and other $C_3$-$C_5$ light hydrocarbons. The typical feed ratio range is about 5 to 20 parts hydrocarbon extractant per part by volume of methanol.

Improved yield of high octane gasoline may be obtained by providing an etherification unit to in conjunction with a large-scale MTG (methanol to gasoline) reaction zone. In the present reactor system, isobutane-rich $C_3$-$C_5$ paraffins from the MTG process may be converted to iso-alkenes. The overall yield of high octane gasoline from oxygenate conversion is significantly increased. In a further improvement, the olefinic methanol-containing vapors are separated from the ether products and coreacted in the MTG reaction zone.

The feedstock for a typical MTG process is lower molecular weight oxygenated organic compound(s). Examples of such compounds are $C_1$-$C_4$ aliphatic alcohols and their ethers It is known in the art to partially convert methanol by dehydration, as in the catalytic reaction over gamma-alumina to produce DME intermediate. Typically, a mixture ($CH_3OH + CH_3—O—CH_3 + H_2O$) is produced by partial dehydration. This reaction can take place in direct conversion of methanol to gasoline (MTG).

The MTG process unit may be a fixed bed type, as disclosed in U.S. Pat. Nos. 3,894,107; 3,928,483; 3,931,349; 4,048,250; etc. In a typical fixed-bed MTG process relatively large amounts of isobutane are produced, e.g., about 8% by weight of hydrocarbons product. In the past, it has been the practice to recover the isobutane fraction without an immediate upgrading step. In fluidized bed MTG operations, isobutane production may be optimized in the range of about 5-10 wt. % of hydrocarbon effluent.

Overall the producton of MTG gasoline plus ethers will increase blended gasoline pool octane because of their high component octanes. Ethene-containing gas from dehydrogenation can be routed directly or indirectly to the MTG unit to react $C_2=$ to gasoline. This will eliminate the need for cryogenic separation required to separate ethene. The desired MTG products are $C_4$ and $C_5$ iso-alkanes, which will ordinarily comprise at least 5% of the recovered product.

Referring to the drawing, a continuous stream of crude methanol (MeOH) feedstock is introduced via conduit 10 with a stream of olefinic hydrocarbon liquid extractant introduced via conduit 12 to extraction separation unit 14, operated at about 35°-40° C. These streams are contacted under liquid extraction conditions to provide an aqueous raffinate phase. An aqueous stream containing a major amount of the water present in the crude feedstock is withdrawn via conduit 16. The lighter organic extract phase containing hydrocarbon extraction solvent and the major amount of feedstock methanol is recovered from extraction unit 14 via conduit 18, and introduced under temperature and process conditions suitable for conversion of methanol in contact with etherification catalyst in reactor 20. Supplemental reactants, such as dry alcohol or iso-alkenes may be added via line 19 to the etherification reaction zone to maintain stoichiometric ratio of reactants as desired. From reactor 30, the effluent stream 22 passes to a debutanizer fractionation tower 30.

In debutanizer separation unit 30 the $C_5+$ tert-alkyl ether product (MTBE and/or TAME) is recovered as a liquid product stream 32, along with unreacted $C_5$ (or optionally heavier $C_6$) hydrocarbons in the extractant. Fractionation tower overhead vapor comprising unreacted $C_4$ hydrocarbons and methanol is removed via conduit 34, and sent is sent to catalytic zeolite conversion unit 40, where it is contacted concurrently with aqueous raffinate from line 16.

The aqueous raffinate stream 16 consists essentially of water, partitioned methanol (e.g.—50-80 wt. %) and a trace of hydrocarbon. This stream is reactive at elevated temperature in the presence of an acid zeolite catalyst, such as medium pore shape selective zeolite, such as, ZSM-5, etc., in a fluidized bed MTG reaction zone to produce predominantly gasoline range liquid hydrocarbons, along with a saturated hydrocarbon intermediate to be treated as herein described.

Effluent stream 42 is condensed and separated by phase and/or fractionation in unit 50 to provide a liquid gasoline product stream 52, byproduct water, light off-gas 54, and a $C_3$-$C_5$ paraffinic intermediate hydrocarbon stream 56, rich in isobutane and isopentane. Dehydrogenation unit 60 converts the intermediate hydrocarbons to an iso-alkene containing liquid suitable for use as an extraction solvent. The dehydrogenation may be achieved catalytically by known unit operations to produce a hydrogen byproduct gas and an olefinic product consisting essentially of $C_2$-$C_5$ olefins. All or a portion of the dehydrogenated aliphatics from unit 60 may be employed as extractant via line 12; however, it is within the inventive concept to separate a portion of these olefins for feeding to conversion unit 40 via line 12A. Paraffinic feed to the deydrogenation unit 60 may be supplemented by various refinery streams via line 62, such as LPG containing propane and butanes.

The aqueous methanol raffinate stream may be coreacted with olefinic light gas and/or other reactive hydrocarbon feedstreams in a conventional MTG reaction section, as described by Tabak in U.S. Pat. No. 4,654,453 and Owen et al in U.S. Pat. No. 4,788,365, incorporated herein by reference. The aqueous methanol may be introduced as a liquid directly to a fluidized bed reaction zone (bottom or middle secton) or vaporized and mixed with effluent vapor from the etherification unit. Optionally, etherification effluent overhead and/or $C_2$-$C_5$ olefinic light hydrocarbon gas containing ethene, propene, unreacted butylenes, etc., may be injected at the bottom of the fluidized bed reaction zone and converted along with the raffinate stream.

EXTRACTION UNIT OPERATION

The typical preferred crude feedstock material is methanol containing about 4 to 17% by weight water. The extraction contact unit may be a stirred multi-stage vertical extraction column adapted for continuous operation at elevated pressure. Any suitable extraction equipment may be employed, including cocurrent, cross-current or single contactors, wherein the liquid methanol feedstock is intimately contacted with a substantially immiscible liquid hydrocarbon solvent, which may be a mixture of $C_4+$ aliphatic components including lower alkanes, n-alkenes or relatively pure isoalkenes, such as isobutylene, etc. This unit operation is described in *Kirk-Othmer Encyclopedia of Chemical Technology* (Third Ed.), 1980, pp. 672-721. Other equipment for extraction is disclosed in U.S. Pat. Nos. 4,349,415 (DeFilipi et al), 4,626,415 (Tabak), and 4,665,237 (Arakawa et al). Unit operation details are also disclosed by Harandi and Owen in U.S. Pat. No. 4,777,321, incorporated herein by reference. The methanol extraction step can be performed advantageously in a countercurrent multistage design, such as a simple packed column, rotating disk column, agitated column with baffles or mesh, or a series of single stage mixers and settlers.

In a typical methanol extraction the crude aqueous feedstock containing about 4% water is contacted with olefinic liquid hydrocarbons in a liquid-liquid contact and separation unit at about 38° C. (100° F.). The extractor unit is operated at about 35°-65° C. (100°-150° F.) and 0-2000 kPa.

ETHERIFICATION OPERATION

The reaction of methanol with isobutylene and isoamylenes at moderate conditions with a resin catalyst is known technology, as provided by R. W. Reynolds, et al., *The Oil and Gas Journal.* Jun. 16, 1975, and S. Pecci and T. Floris, *Hydrocarbon Processing,* December 1977. An article entitled "MTBE and TAME—A Good Octane Boosting Combo", by J. D. Chase, et al., *The Oil and Gas Journal,* Apr. 9, 1979, pages 149–152, discusses the technology. A preferred catalyst is a sulfonic acid ion exchange resin which etherifies and isomerizes the reactants. A typical acid catalyst is Amberlyst 15 sulfonic acid resin.

Processes for producing and recovering MTBE and other methyl tert-alkyl ethers for $C_4$-$C_7$ isoolefins are known to those skilled in the art, such as disclosed in U.S. Pat. No. 4,788,365 (Harandi and Owen). Various suitable extraction and distillation techniques are known for recovering ether and hydrocarbon streams from etherication effluent.

CONVERSION OF METHANOL AND HYDROCARBONS TO LIQUID HYDROCARBONS

Zeolite catalysis technology for upgrading lower aliphatic hydrocarbons and oxygenates to liquid hydrocarbon products are well known. Commerial Methanol-to-Gasoline (MTG), methanol-to olefins (MTO), aromatization (M2-Forming) and Mobil Olefin to Gasoline/Distillate (MOG/D) processes employ shape selective medium pore zeolite catalysts for these processes. It is understood that the present zeolite conversion unit operation can have the characteristics of these catalysts and processes to produce a variety of hydrocarbon products, especially liquid aliphatic and aromatics in the $C_5$-$C_9$ gasoline range.

DESCRIPTION OF ZEOLITE CATALYST

Recent developments in zeolite technology have provided a group of medium pore siliceous materials having similar pore geometry. Most prominent among these intermediate pore size zeolites is ZSM-5, which is usually synthesized with Bronsted acid active sites by incorporating a tetrahedrally coordinated metal, such as Al, Ga, Fe or mixtures thereof, within the zeolitic framework. These medium pore zeolites are favored for acid catalysis; however, the advantages of ZSM-5 structures may be utilized by employing highly siliceous materials or cystalline metallosilicate having one or more tetrahedral species having varying degrees of acidity. ZSM-5 crystalline structure is readily recognized by its X-ray diffraction pattern, which is described in U.S. Pat. No. 3,702,866 (Argauer, et al.), incorporated by reference.

Zeolite hydrocarbon upgrading catalysts preferred for use herein include the medium pore (i.e., about 5-7A) shape-selective crystalline aluminosilicate zeolites having a silica-to-alumina ratio of at least 12, a constraint index of about 1 to 12 and acid cracking activity (alpha value) of about 1-250, preferably about 3 to 80 based on total catalyst weight. In the fluidized bed reactor the coked catalyst may have an apparent activity (alpha value) of about 3 to 80 under the process conditions to achieve the required degree of reaction severity. Representative of the ZSM-5 type medium pore shape selective zeolites are ZSM-5, ZSM-11, ZSM-12, ZSM-22, ZSM-23, ZSM-35, and ZSM-48. Aluminosilicate ZSM-5 is disclosed in U.S. Pat. No. 3,702,886 and U.S. Pat. No. Re. 29,948. Other suitable zeolites are disclosed in U.S. Pat. Nos. 3,709,979; 3,832,449; 4,076,979; 3,832,449; 4,076,842; 4,016,245; 4,414,423; 4,417,086; 4,517,396 and 4,542,251. The disclosures of these patents are incorporated herein by reference. While suitable zeolites having a coordinated metal oxide to silica molar ratio of 20:1 to 200:1 or higher may be used, it is advantageous to employ a standard ZSM-5 having a silica alumina molar ratio of about 25:1 to 70:1, suitably modified if desired to adjust acidity and oligomerization/aromatization characteristics. A typical zeolite catalyst component having Bronsted acid sites may consist essentially of aluminosilicate ZSM-5 zeolite with 5 to 95 wt. % silica and/or alumina binder.

Usually the zeolite crystals have a crystal size from about 0.01 to 2 microns or more. In order to obtain the desired particle size for fluidization in the turbulent regime, the zeolite catalyst crystals are bound with a suitable inorganic oxide, such as silica, alumina, etc. to provide a zeolite concentration of about 5 to 95 wt. %. It is advantageous to employ a standard ZSM-5 having a silica:alumina molar ratio of 25:1 or greater in a once-through fluidized bed unit to convert 60 to 100 percent, preferably at least 75 wt. %, of the monoalkenes and methanol in a single pass. In the preferred embodiment 25% H-ZSM-5 catalyst calclined with 75% silica-alumina matrix binder is employed unless otherwise stated.

Particle size distribution can be a significant factor in achieving overall homogeneity in turbulent regime fluidization. It is desired to operate the process with particles that will mix well throughout the bed. Large particles having a particle size greater than 250 microns should be avoided, and it is advantageous to employ a particle size range consisting essentially of 1 to 150 microns. Average particle size is usually about 20 to 100 microns, preferably 40 to 80 microns. Particle distribution may be enhanced by having a mixture of larger and smaller particles within the operative range, and it is particularly desirable to have a significant amount of fines. Close control of distribution can be maintained to keep about 10 to 25 wt. % of the total catalyst in the reaction zone in the size range less than 32 microns. Accordingly, the fluidization regime is controlled to assure operation between the transition velocity and transport velocity.

FLUIDIZED BED MTG REACTOR OPERATION

In addition to the aqeuous methanol an olefinic components of the reactor feed, suitable oxygenate and or olefinic supplemental feedstreams may be added to the preferred MTG reactor unit. Non-deleterious components, such as lower paraffins and inert gases, may be present. The reaction severity conditions can be controlled to optimize yield of $C_3$-$C_5$ paraffins, olefinic gasoline or $C_6$-$C_8$ BTX hydrocarbons, according to product demand. It is understood that aromatic hydrocarbon and light paraffin production is promoted by those zeolite catalysts having a high concentration of Bronsted acid reaction sites. Accordingly, an important criterion is selecting and maintaining catalyst inventory to provide either fresh or regenerated catalyst having the desired properties. Reaction temperatures and contact time are also significant factors in the reaction severity, and the process parameters are followed to give a substantially steady state condition wherein the reaction severity is maintained within the limits which yield a desired weight ratio of propane to propene in the reaction effluent.

In a turbulent fluidized catalyst bed the conversion reactions are conducted in a vertical reactor column by passing hot reactant vapor or lift gas upwardly through the reaction zone at a velocity greater than dense bed transition velocity and less than transport velocity for the average catalyst particle. A continuous process is operated by withdrawing a portion of coked catalyst from the reaction zone, oxidatively regenerating the withdrawn catalyst and returning regenerated catalyst to the reaction zone at a rate to control catalyst activity and reaction severity to effect feedstock conversion.

Upgrading of olefins by such hydrogen contributors in co-conversion reactors is taught by Owen et al in U.S. Pat. Nos. 4,788,365 and 4,090,949, and in application Ser. No. 179,726, filed Apr. 11, 1988, incorporated herein by reference. In a typical process, the methanol and olefinic feedstreams are converted in a catalytic reactor under elevated temperature conditions and moderate pressure (i.e.—100 to 2500 kPa) to produce a predominantly liquid product consisting essentially of $C_6^+$ hydrocarbons rich in gasoline-range paraffins and aromatics. The reaction temperature can be carefully controlled in the usual operating range of about 250° C. to 650° C., preferably at average reactor temperature of 350° C. to 500° C.

DEHYDROGENATION PROCESS OPERATION

An important unit operation in the conversion of iso-paraffins to their corresponding iso-olefins is dehydrogenation. Conventionally this can be achieved by high temperature cracking using hydrogenation-dehydrogenation catalyst; however, it is within the inventive concept to employ transhydrogenation in this process step to effect removal of hydrogen from the $C_3$–$C_5$ intermediate alkanes. Various processes are known for producing isoalkene-rich by dehydrogenation (including isomerization processes), such as discloses in U.S. Pat. No. 4,393,250 (Gottlieb et al). Typical processes are operated at elevated temperature (about 530°–700° C.) and moderate pressure using an active alumina solid catalyst impregnated with Pt or Cr oxide. Other dehydrogenation techniques are disclosed in *Oil & Gas Journal*, Dec. 8, 1980, pp. 96–101; *Hydrocarbon Processing*, Apr. 1982, pp. 171–4; U.S. patent application Ser. No. 179,729, filed Apr. 11, 1988, and in U.S. Pat. No. 4,216,346 (Antos).

The present invention is particularly advantageous in the economic dewatering of crude methanol, thus avoiding expensive and energy-intensive prefractionation by distillation. By extracting methanol from the crude feedstock with olefinic hydrocarbon reactant liquid, substantial utilities and equipment savings are realized. Various modifications can be made to the system, especially in the choice of equipment and non-critical processing steps.

While the invention has been described by specific examples, there is no intent to limit the inventive concept is set forth in the following claims.

We claim:

1. A continuous feedstock separation and etherification reactor system for converting crude methanol feedstock to methyl t-alkyl ether comprising:

extraction means for contacting crude feedstock liquid containing a minor amount of water with a liquid olefinic hydrocarbon extraction solvent stream under extraction conditions favorable to selective extraction of methanol, thereby providing an extract liquid stream rich in methanol and an aqueous raffinate stream lean in methanol;

first catalytic reactor means operatively connected to said extraction means for contacting the extract stream in a catalytic reaction zone with acid etherification catalyst in an etherification reaction zone under process conditions to convert a major portion of methanol to ether;

effluent separation means operatively connected to said first catalyst reactor means for recovering ether product from unconverted olefinic hydrocarbon and methanol and second catalyst reactor means operatively connected to said effluent separation means for contacting said raffinate stream with conversion catalyst in the presence of said unconverted olefinic hydrocarbon and methanol to produce normally liquid $C_6^+$ gasoline product along with saturated $C_5^-$ intermediate hydrocarbon;

means for recovering a gasoline product stream and saturated intermediate hydrocarbon stream from a second catalytic reactor effluent;

third reactor means operatively connected to said means for recovering a gasoline product stream and saturated intermediate hydrocarbon stream for dehydrogenating said $C_5$ intermediate hydrocarbon to produce an olefin liquid stream rich in isoalkene; and means for recovering and recycling the olefinic liquid stream from third reactor means to the extractor means for use as extraction solvent.

2. A continuous catalytic reactor system operatively connected for converting oxygenate feedstock to liquid hydrocarbon comprising:

primary reactor means containing acid shape selective medium pore zeolite catalyst for converting oxygenate feedstock to predominantly gasoline range hydrocarbons and thereby producing a minor amount of isobutane;

separation means operatively connected to said primary reactor means for receiving and recovering $C_6^+$ gasoline product and isobutane-rich $C_5^-$ paraffinic intermediate hydrocarbons from primary reactor means effluent;

dehydrogenation reactor means operatively connected to said separation means for receiving and converting paraffinic intermediate predominantly to $C_2$–$C_5$ lower olefins comprising isobutylene;

means for recovering an isobutylene-rich olefinic stream from the dehydrogenation reactor means operatively connected to said dehydrogenation reactor means;

means for passing the isobutylene-rich olefinic stream and a lower aliphatic alcohol stream to an etherification reactor means containing etherification catalyst operatively connected to said means for passing the isobutylene-rich olefinic stream and a lower aliphatic alcohol stream for conversion of isoalkene to tertiary-alkyl ether; and fractionator means operatively connected to said means for passing the isobutylene-rich olefinic stream and a lower aliphatic alcohol stream for recovering liquid ether product and overhead vapor containing unreacted alcohol and $C_4+$ olefins from the etherification reactor zone; and means for feeding said overhead vapor to said primary reactor means operatively connected to said fraction for means for coconversion with oxygenate feedstock.

3. The system of claim 2 wherein catalyst in the primary reactor means comprises acid ZSM-5.

4. The system of claim 2 wherein the primary reactor means comprises a fluidized bed of fine catalyst particles maintained in a vertical reactor shell; and means for introducing factionator overhead vapor below the catalyst bed for upward flow therethrough.

* * * * *